United States Patent [19]

Mitchell et al.

[11] Patent Number: 5,153,310

[45] Date of Patent: Oct. 6, 1992

[54] IL-2 ANALOGS CONTAINING N-LINKED GLYCOSYLATION SITES

[75] Inventors: Kenneth F. Mitchell; Carol A. Vallone, both of Media, Pa.

[73] Assignee: Du Pont Merck Pharmaceutical Company, Wilmington, Del.

[21] Appl. No.: 317,177

[22] Filed: Feb. 28, 1989

[51] Int. Cl.⁵ .............................. C07K 13/00
[52] U.S. Cl. ................... 530/351; 530/395; 435/69.52
[58] Field of Search .............. 530/351, 395; 435/69.52

[56] References Cited

PUBLICATIONS

Hofer et al., *Biol. Chem. Hoppe Seyler* 368(9):1060 (1987).
Ju et al., *J. Biol. Chem.* 262:5723–5731 (1987).
Liang et al., *J. Biol. Chem.* 261:334–337 (1986).
Cohen et al., *Science* 234:349–352 (1986).
Wang et al., *Science* 224:1431–1433 (1984).
Bio-Rad Catalog No. 170-3571.
Kunkel *Proc. Natl. Acad. Sci.* 82:488–492 (1985).
Ferrara et al., *FEBS* 226(1), pp. 47–52 (1987).

*Primary Examiner*—David L. Lacey
*Assistant Examiner*—Shelly J. Guest
*Attorney, Agent, or Firm*—Blair Q. Ferguson; Don M. Kerr

[57] ABSTRACT

Biologically active analogs of human IL2, which differ from natural IL2 by the substitution of amino acid residues to form N-linked glycosylation sites in the molecule, are prepared by recombinant DNA techniques. Such analogs of IL2 are N-linked glycosylated when expressed in eukaryotic cells. Natural IL2 is not N-linked glycosylated.

12 Claims, No Drawings

IL-2 ANALOGS CONTAINING N-LINKED GLYCOSYLATION SITES

FIELD OF THE INVENTION

The present invention concerns proteins derived by molecular cloning and microbial expression in cell culture. In particular, the invention relates to the production of altered, biologically active forms of human interleukin 2 (IL2) that differ in sequence from natural IL2 by the substitution of amino acid residues to form N-linked glycosylation sites which are glycosylated when the molecule is expressed in eukaryotic cells.

BACKGROUND OF THE INVENTION

Interleukin 2 (IL2) is a protein secreted by lymphocytes and belongs to the class of immune modulating substances called lymphokines. IL2 was first described as T-cell growth factor (TCGF), a lymphokine capable of promoting the proliferation of T lymphocytes (Morgan et al. (1976) *Science* 193, 1007-1008; Ruscetti et al. (1977) *J. Immunol.* 119, 131-138). IL2 has been shown to modulate many other immunological effects on lymphoid cells including cytotoxic T-cells, natural killer cells, activated B-cells, and lymphokine activated killer (LAK) cells (Robb (1984) *Immunol. Today* 5, 203 and references therein). IL2 is used to generate LAK cells that kill fresh tumor cells but not normal cells (Grimm et al. (1982) *J. Exp. Med.* 155, 1823-1841; Mazumder et al. (1984) *J. Exp. Med.* 159, 495-507). Recently, treatment of cancer patients by administration of IL2 and autologous LAK cells has demonstrated the potential use of IL2 as an immunotherapeutic agent (Rosenberg et al. (1985) *N. Eng. J. Med.* 313, 1485-1492).

Molecular cloning of the human IL2 cDNA (Taniguchi et al. (1983) *Nature* 302, 305-310; Deves et al. (1983) *Nucleic Acids Res.* 11 4307-4323) has allowed determination of the primary sequence structure of IL2 and the production of large amounts of biologically functional IL2 using heterologous expression systems, including *E. coli* systems (Ju et al. (1987) *J. Biol. Chem.* 262 5723-5731 and references therein). Molecular cloning procedures have been used to produce structurally altered forms of IL2 with substitutions and deletions of amino acid residues (Ju et al. op. cit. and references therein). By examining the effects of these structural alterations on the function of IL2, regions of the IL2 protein important for its function have been identified. Biologically functional IL2-derived proteins containing additional amino acid residues at the N-terminus of IL2 have also been reported (Takeda patent EP 1058198; Murphy patent WO 86/0090; Sandoz patent EP 0163603). Previous references show that small deletions or substitutions at the C-terminus of IL2 result in loss of functional activity (Ju et al. op. cit.; Liang et al. (1986) *J. Biol. Chem.* 261, 334-337).

The present invention provides structurally altered, biologically functional forms of IL2 wherein amino acid residues are substituted within the molecule in such a way as to create N-linked glycosylation sites that are effectively glycosylated when the molecule is expressed in eukaryotic cells.

Recombinant IL2 analogs having potential N-glycosylation sites have been reported in Hofer et al. (1987) *Biol. Chem. Hoppe-Seyler* 368 (9), 1060. Potential N-glycosylation sites were created by substituting Asn for Thr-3, Lys-97, Glu-100, Asp-109 or Cys-125. In only one case (Asn for Glu-100) was N-glycosylation observed. Amino acid positions 3, 97, 100, 109 and 125 in the numbering system used by Hofer et al. correspond to positions 4, 98, 101, 110 and 126 in the numbering system used in this application.

SUMMARY OF THE INVENTION

This invention provides recombinant IL2 analogs which have substantially the same spectrum of biological activity and substantially the same amino acid sequence as native human mature IL2, but which differ from native human mature IL2 in that they have one or more amino acid substitutions to provide one or more N-linked glycosylation sites NXT or NXS, where in X is any amino acid except D, W or P. The recombinant IL2 analogs of this invention differ from those of Hofer et al, id., in that the N of the glycosylation site or sites occurs at one or more of amino acid positions 5, 6, 9, 36, 50, 72, 74, 78, 86, 89, 91, 100, 112, and 132, wherein the position numbers correspond to the numbers for r-IL2 as shown in Table 1 of this application, and the sites are effectively recognized and glycosylated when the molecule is expressed in a eukaryotic cell host.

These biologically functional analogs of IL2 are obtained by molecular cloning and expression of recombinant DNA in prokaryotic or eukaryotic cells. They are obtained in a nonglycosylated form when expressed in a prokaryotic cell host or in a glycosylated form when expressed in a eukaryotic cell host.

Both the glycosylated and nonglycosylated forms of these analogs retain substantially the same spectrum of biological activity as natural human IL2, that is, they retain the ability to bind IL2 receptors, stimulate T cell growth and proliferation, and generate LAK cells. Consequently, they can be used in any device or therapy in which natural human IL2 is used. In addition, it is believed that the N-linked glycosylated analogs may exhibit increased serum retention compared to natural human IL2. In addition, it is expected that post-translational, in vitro enzymatic addition of sialic acid to carbohydrate side chains of the analogs may further increase serum half-life and improve in-vivo efficacy.

The analogs contain substantially the same amino acid sequence as natural human IL-2, but they may differ from natural human IL2 in ways other than the incorporation of one or more N-linked glycosylation sites. For example, they may contain the mutations described in Ju et al. op. cit. and in Mark et al., U.S. Pat. No. 4,518,584, the disclosures of which are incorporated herein. In general, they may have internal amino acid deletions, additions or substitutions and they may have N-terminal leaders and/or C-terminal extensions, such as the leaders and extensions described below.

DETAILED DESCRIPTION OF THE INVENTION

Several derivatives of IL2 have been produced in *E. coli* and mammalian cells using molecular cloning procedures. In human cells, human IL2 is expressed as a precursor protein that is proteolytically cleaved to produce the mature biologically functional form of IL2 (Taniguchi et al., op. cit.; Robb et al. (1983) *Proc. Natl. Acad. Sci.* 80, 5990–5994). This form of human cell-expressed IL2, designated mature IL2, has an N-terminal Ala residue and is 133 amino acid residues in length. The amino acid residues and corresponding codons of mature IL2 are here designated throughout as amino acid 2 to amino acid 134 as shown in Table 1 below. The E. coli expression vector, and the designation and the structure of the IL2-derived protein encoded by the E. coli expression vector are indicated below in Table 1. The IL2 derivatives expressed in E. coli contain an N-terminal Met (designated here as amino acid 1) initially following translation, however, this Met residue may be subsequently proteolytically removed in E. coli by methionine amino peptidases. N-terminal sequencing of purified r-IL2 has shown that the N-terminal Met is removed in approximately 50% of the molecules purified from E. coli.

TABLE 1

| Plasmid | Protein | Protein sequence |
|---|---|---|
| pTrpE-IL2 | r-IL2 | 2      118      134<br>\|         \|        \|<br>MAP . . . FLNRWITFCQSIISTLT |
| pTrpGk | L-IL2 | 148<br>\|<br>MAP . . . FLNRWITFCQSIISTGTGGGKKDKKDKKDLE |
| Mature, human IL2 | | AP . . . FLNRWITFCQSIISTLT<br>\|                \|<br>2              134 |

The molecular cloning and E. coli expression procedures are detailed in Example 1 and Example 2. The construction of plasmid pTrpE-IL2 (ATCC No. 59754) and pTrpGk (ATCC No. 67540) and the expression in E. coli of r-IL2 and L-IL2 are detailed in DeVries et al., copending patent application U.S. Ser. No. 07/128931, the disclosure of which is incorporated herein, now abandoned. The 14 amino acid C-terminal extension of IL2 in L-IL2, (Gly)3-(Lys-Lys-Asp)3-Leu-Glu, was specifically designed to facilitate the solubilization of the protein or the derivatization of the protein to a solid support. The coding sequence and encoded amino acid sequence for L-IL2 are shown in Table 9 below. L-IL2 retains the full biological activities of natural IL2; L-IL2 supports the proliferation of T-cells, augments NK cell activity and induces LAK activity.

In order to introduce N-linked glycosylation sites into the IL2 molecule we used site-specific mutagenesis with synthesized oligonucleotides to alter the IL2 DNA coding sequence, such that the encoded IL2 analog contained amino acid substitutions that formed part of an N-linked glycosylation site. The N-linked glycosylation site is defined by the occurrence in the protein of the sequence NXT or NXS (reading from N-terminal to C-terminal), where X =any amino acid except D, W, or P. Abbreviations used for amino acid residues are given below. N-linked glycosylation sites do not naturally occur in human IL2. If the N-linked glycosylation site is appropriately positioned in the protein molecule, such that it is accessible to and recognized by the appropriate glycosylation enzymes during co-translational and post-translational biosynthesis of the protein, then the protein will be N-linked glycosylated at the N residue within the N-linked glycosylation site.

Our goal was to select regions and specific sites in the IL2 molecule where amino acid substitutions forming N-linked glycosylation sites could be introduced without interfering with the functional activity of the protein, including its ability to function as TCGF and to generate LAK cells. Sites and regions within IL2 that were likely to meet this standard were identified using the following criteria:

1) An evolutionary comparison study was performed. The published IL2 DNA sequences of bovine (Cerretti et al. Proc. Natl. Acad. Sci. U.S.A. 1986 83:3223-3227), murine (Kashima et al. Nature (1985) 313:402-404), and human (Taniguchi et al., op, cit.) origin were compared to identify conserved and variable regions in the gene.

2) We examined recently published antibody binding studies (Robb, Immunology Today (1984) 5:203-209; Kuo and Robb, J. Immunology (1986) 137:1538-1543; Altman et al. Proc. Natl. Acad. Sci. U.S.A. (1984) 81:2176-2180) where human IL2 protein was tested for biological activity in the presence of antibodies, each of which recognize a 10 to 30 residue region of the molecule, to identify areas of IL2 that may be directly associated with activity.

3) Recently published point mutation/deletion studies (Ju J. Biol. Chem. (1987) 262:5723-5731; Cohen et al. Science (1986) 234:349-352; Liang et al. J. Biol. Chem. (1986) 261:334-337; Wang et al. Science (1984) 224:1431-1433) where amino acids of human IL2 were changed or deleted by site-specific mutagenesis and the encoded IL2-derived proteins were tested for biological activity, were also examined to identify mutation tolerant regions and regions intolerant to change.

Based on this examination, we have identified several regions within the IL2 molecule that are predicted to be tolerant to amino acid substitution changes. That is, regions were identified where amino acid substitutions may be introduced without appreciable loss of biological activity of the molecule.

We then considered the locations in terms of whether acceptable amino acid changes could be made which would generate a glycosylation site at that point. Our judgment was guided by whether the required amino acid changes were conservative, whether the region was conserved and whether or not the particular amino acids were likely to be involved in forming important secondary structural features. Based on these criteria we identified amino acid position numbers 5, 6, 9, 27, 36, 50, 72, 74, 78, 86, 89, 91, 100, 101, 112 and 132 as sites having a high probability of yielding an active glycosylated product. Again, position 101 in our numbering system corresponds to position 100 in the numbering system used by Hofer et al.

Within these regions, we have introduced specific amino acid substitutions in order to form the appropriate N-linked glycosylation site. These amino acid substitutions are shown below in Table 2.

TABLE 2

| Amino Acid Substitutions in IL2 Forming N-linked Glycosylation Sites | | | | |
|---|---|---|---|---|
| Amino Acid | Wild Type Amino Acid | Substituted Amino Acid | Designation of Substitution | Site Glycosylated |
| 6 | S | N | N6 | N6 |
| 29 | I | S | S29 | N27 |
| 80 | H | T | T80 | N78 |

TABLE 2-continued

| | Amino Acid Substitutions in IL2 Forming N-linked Glycosylation Sites | | | |
|---|---|---|---|---|
| Amino Acid | Wild Type Amino Acid | Substituted Amino Acid | Designation of Substitution | Site Glycosylated |
| 91 | N | T | T91 | N89 |
| 132 | T | N | N132 | N132 |

A series of IL2 analogs were constructed that contain substitutions at two or more of the sites shown in Table 2. Thus, these analogs of IL2 have two or more N-linked glycosylation sites. These IL2 analogs with two or more substitutions are listed in Table 3.

TABLE 3

| IL2 Analogs with Two or More N-linked Glycosylation Sites |
|---|
| N6/S29 |
| N6/T80 |
| N6/T91 |
| N6/N132 |
| N6/T91/N132 |

The substitutions indicated in Table 4 have been introduced into both native sequence IL2 (r-IL2) and L-IL2. Thus, the N6 substitution is designated IL2-N6-L; the native sequence IL2-derived protein with the N6 substitution is designated IL2-N6.

The following conventional one- and three-letter amino acid abbreviations are used:

A = Ala = Alanine
C = Cys = Cysteine
D = Asp = Aspartic acid
E = Glu = Glutamic acid
F = Phe = Phenylalanine
G = Gly = Glycine
H = His = Histidine
I = Ile = Isoleucine
K = Lys = Lysine
L = Leu = Leucine
M = Met = Methionine
N = Asn = Asparagine
P = Pro = Proline
Q = Gln = Glutamine
R = Arg = Arginine
S = Ser = Serine
T = Thr = Threonine
V = Val = Valine
W = Trp = Tryptophan
Y = Tyr = Tyrosine
B = Asx = Asp or Asn, not distinguished
Z = Glx = Glu or Gln, not distinguished, or pyrrolidone carboxylic acid
X = X = Undetermined or atypical amino acid

EXAMPLES

The invention is further described by the following Examples, wherein all parts and percentages are by weight and degrees are Celsius.

EXAMPLE 1

Plasmid Constructions

Plasmid constructions were carried out using standard methodology as described by Maniatis et al., *Molecular Cloning: A Laboratory Manual*, Cold Spring Harbor Laboratory, N.Y. (1982), the teaching of which is hereby incorporated by reference. Enzymes and other reagents used for plasmid constructions were obtained from Bethesda Research Laboratories, Gaithersburg, Md. or New England Biolabs, Beverly, Mass. Methods for digesting, identifying, recovering, and purifying the various nucleotide sequences used in the invention are known to those skilled in the art as are methods for ligating the sequences into vectors, transforming host microorganism strains, cloning, and recovering products synthesized. Accordingly, the methods will only be described by reference to specific embodiments of the invention set forth hereinafter. Oligonucleotides were synthesized on an Applied Biosystems DNA synthesizer using procedures recommended by the supplier.

Plasmid pTrpGk encodes an IL2-derived protein differing from natural IL2 by the replacement of the C-terminal Leu-Thr residues by the sequence:

Gly-Thr-Gly$_3$-(Lys-Lys-Asp)$_3$-Leu-Glu. This IL2 derivative with a Lys-rich 14 aa C-terminal extension is designated L-IL2. The coding sequence and encoded amino acid sequence for L-IL2 are shown in Table 9. In plasmid pTrpGk, the expression of the product L-IL2 is under the transcriptional control of the *E. coli* trp operon promoter.

Plasmid pTrpE-IL2 expresses the mature form of human IL2 in *E. coli* under the transcriptional control of the trp operon promoter. The product of pTrpE-IL2 is designated r-IL2. *E. coli*-expressed mature IL-2 (r-IL2) differs from human cell-expressed mature IL-2 by the addition of an N-terminal Met residue. Approximately 50% of mature human IL2 expressed in *E. coli* has the N-terminal Met residue specifically removed by the action of aminopeppidases in *E. coli*. The sequence of mature human IL2 expressed in *E. coli* from pTrpE-IL2 is indicated in Table 1.

Oligonucleotide directed in vitro mutagenesis was carried out using the Muta-Gene in vitro mutagenesis kit (Bio-Rad, Catalog No. 170-3571) according to the method of Kunkel (*Proc. Natl. Acad. Sci.* (1985) 82:488-492). Other standard procedures for site-directed mutagenesis may be used (Botstein and Shortle (1985) *Science* 229:74-79). The HindIII to BamHI fragment of pTrpGk containing the L-IL2 coding sequence (Table 9) was inserted into the M13mp18 phage vector to yield recombinant phage M13-L-IL2. M13-L-IL2 was grown in CJ236 (dut$^-$, ung$^-$) to produce a uracil containing single-stranded DNA template for mutagenesis. The single-stranded M13-L-IL2 DNA was annealed with a synthetic oligonucleotide containing a desired base change. The oligonucleotides used to construct the various IL2 analogs of the invention are listed in Table 4.

TABLE 4

| Oligonucleotides for Mutagenesis |
|---|
|                 SpeI |
| N6    GCT CCT ACT <u>AGT AAT</u> TCT ACA AAG |
| S29   TTT TGA ATG GAA GTA ATA ATT ACA AG |

TABLE 4-continued
Oligonucleotides for Mutagenesis

```
                                          BclI
                                           |
T80    GCA AAA ACT TTA CCT TAA GAC CCA GGG ACT TGA TCA GC

BclI
          |
T91    CAG GGA CTT GAT CAG CAA TAT CAC CGT AAT AGT TC

N132   CAT CAT CTC AAA CGG TAC CGG AG
```

Following annealing and elongation using T4 DNA ligase and T4 polymerase to create double-stranded DNA, the uracil-containing double-stranded M13-L-IL2-derived DNA was used to transform *E. coli* strain MVI190 (dut+, ung+). The resultant plaques were picked and single-stranded M13-L-IL2-derived DNA was prepared and sequenced to confirm the introduction of the desired nucleotide change. The resultant M13-L-IL2 derived DNAs are designated M13-N6, M13-S29, M13-T80, M13-T91, and M13-N132. As indicated in Table 4, the oligonucleotide used to generate the N6 substitution also introduced a unique SpeI site and the oligonucleotides used to generate the T80 and T91 substitutions introduced unique BclI sites.

The resultant mutagenized HindIII to BamH1 DNA fragment containing the L-IL2-derived coding sequence was excised from the M13 vector and ligated to the BamHI to HindIII trp promoter-containing fragment of plasmid pKGP36-trp (Ivanoff et al. (1986) *Proc. Natl. Acad. Sci.* 83:5392–5396; ATCC No. 39413). Plasmid expression vector pKGP36-trp provides transcriptional control signals derived from the *E. coli* trp operon, as well as translation initiation signals. The resultant plasmids are designated ptrp-N6-L, ptrp-S29-L, ptrp-T80-L, ptrp-T91-L, and ptrp-N132-L. The pKGP36-trp derivative expresses the mature form IL2 analog in *E. coli* under the control of the trp operon promoter.

A second round of oligonucleotide directed mutagenesis was performed on M13-S29, M13-T80, M13-T91, and M13-N132, as described above, using the N6 oligonucleotide shown in Table 4, to generate a series of M13 derivatives encoding IL2 analogs, each of which contained the N6 substitution and a unique non-naturally occurring SpeI site which was introduced as a silent mutation without altering the encoded amino acid sequence. The resultant M13-IL2-derived DNAs are designated M13-N6/S29, M13-N6/T80, M13-N6/T91, M13-N6/N132.

In addition, M13-N6 was used with the T91 and N132 oligonucleotides shown in Table 4 to generate M13-N6/TgI/N132, also containing the SpeI site. Plasmid ptrp-N6/S29-L was constructed by ligation of the HindIII to BamHI DNA fragment of M13-N6/S29 containing the L-IL2-derived coding sequence with the BamH1 to HindIII trp promoter-containing fragment of pKGP36-trp.

An approximately 100 bp "leader" DNA fragment, encoding the IL2 N-terminal leader peptide that directs the protein to the protein secretory pathway, was made by synthesizing and annealing 4 oligonucleotides. This DNA fragment was inserted between the HindIII and EcoRI sites of pUC19, to yield plasmid pLDR. The sequence of the leader DNA fragment is shown below. The position of restriction endonuclease sites, the codon for the N-terminal Ala residue of mature IL2 and the N-terminal Met of pro-IL2 are indicated.

```
   H
   i
   n
   d
   I
   I                        Met
   I                         |
      a g C T t  CCACA ATG TAC AGG ATG CAA CTC CTG TCT TGC ATT GCA CTA AGT
  1 ---------------+-- ---- ---- ---+ ---- ---- ---- +--- ---- ----  -+-- ---- ---- ---+  50
            a GGT GT TAC ATG TCC TAC GTT GAG GAC AGA ACG TAA CGT GAT TCA

S           K           H
                                                         p           p           p
                                              Ala        e           n           a
                                               |         I           I           I
      CTT GCA CTT GTC ACA AAC AGT GCA CCT ACT a g t  g g t  a c c  t g a  t a a  g t t  a a
 51 ---- ---- ---- +--- ---- ----  -+-- ---- ----+ ---- ---- ---- +--- ---- ---- --+ 100
      GAA CGT GAA CAG TGT TTG TCA CGT GGA TGA t c a  c c a  t g g  a c t  a t t  c a a  t t

E
         S       c
         m       o
         a       R
         I       I
         c c c g g g g
   101 -------------+---- 112
         g g g c c c c t t a a
```

The SpeI site in M13-N6, M13-N6/S29, M13-N6/TBO, M13-N6/T91, M13-N6/N132, and M13-N6/T91/N132 was used to provide a unique site at the 5' end of the IL2 coding sequence allowing removal of the sequence encoding the N-terminal Met, which had been engineered into the coding sequence to allow bacterial expression of mature form IL2 and IL2 analogs (as in the ptrp plasmids described above) (see Table 9). As described below, the SpeI site was used to fuse the IL2 analog coding sequence in the M13 vector in-frame with the coding sequence for the IL2 N-terminal leader peptide. The leader peptide is essential for the correct processing and secretion of IL2 in mammalian cells.

The 100 bp leader DNA fragment also contains a SpeI site which allows the mutant IL2 coding sequences to be inserted at the SpeI site to thereby regenerate the complete 5' coding sequence for pro-IL2, keeping the insert in-frame with the leader coding sequence. The synthetic DNA fragment in pLDR also contains a 15 bp sequence between the KpnI site and the SmaI site to provide completion of the coding sequence and stop codons (for those mutants that were to be cut with SpeI and KpnI to remove the Lys-tail). The SpeI to SmaI DNA fragment of the IL2 analog coding sequence retains the Lys-tail and stop codons. See Table 9 for the position of the KpnI and SmaI sites in the L-IL2 coding sequence.

The IL2 analog coding sequences in the above M13 vectors were then excised as a SpeI to KpnI fragment (Lys-tail removed) or as a SpeI to SmaI fragment (Lys-tail included) and inserted into plasmid pLDR to yield a set of plasmids designated pUC-N6, pUC-N6/S29, pUC-N6/T80, pUC-N6/T91, pUC-N6/N132, and pUC-N6/T91/N132 and another set of plasmids designated pUC-N6-L, pUC-N6/S27-L, pUC-N6/T80-L, pUC-N6/T91-L, pUC-N6/N132-L, and pUC-N6/T91/N132-L. The structures of the plasmid constructs were confirmed by DNA sequencing.

The mutant IL2 coding sequences in the pUC-derived plasmids were excised as a HindIII to SmaI DNA fragment and the fragment was ligated to the HindIII to HpaI HIV-1 LTR-containing fragment of p5'LTR-cat. In these plasmids, the complete proform IL2 analog coding sequence (including the sequence encoding the N-terminal leader peptide) is placed under the transcriptional control of the HIV-1 LTR. The resultant plasmids were given the designations listed under "Mammalian Cell Expression" in Table 4. The expression of native sequence IL2 in human cells using the HIV-1 LTR and trans-acting positive-acting HIV-1 tat gene product is detailed in Ferguson et al., copending commonly-assigned patent application U.S. Ser. No. 07/051970, now abandoned, the disclosure of which is incorporated herein.

The recombinant M13 phages and plasmids used to express various IL2 analogs in *E. coli* and mammalian cells are summarized below in Table 5.

TABLE 5
Summary of Recombinant M13 and Plasmids Used to Express IL2 Analogs in *E. Coli* and Mammalian Cells

| | M13 Mutagenesis | |
|---|---|---|
| M13-L-IL2 | M13-N6 | |
| | M13-S29 | M13-N6/S29 |
| | M13-T80 | M13-N6/T80 |
| | M13-T91 | M13-N6/T91 |
| | M13-N132 | M13-N6/N132 |
| | | M13-N6/T91/N132 |

| *E. Coli* Expression | |
|---|---|
| ptrp-N6-L | ptrp-N6/S29-L |
| ptrp-S29-L | ptrp-N6/T80-L |
| ptrp-T80-L | |
| ptrp-T91-L | |

TABLE 5-continued
Summary of Recombinant M13 and Plasmids Used to Express IL2 Analogs in *E. Coli* and Mammalian Cells ptrp-N132-L

| Mammalian Cell Expression | |
|---|---|
| pLTR-N6 | pLTR-N6-L |
| pLTR-N6/S29 | pLTR-N6/S29-L |
| pLTR-N6/T80 | pLTR-N6/T80-L |
| pLTR-N6/T91 | pLTR-N6/T91-L |
| pLTR-N6/N132 | pLTR-N6/N132-L |
| pLTR-N6/T91/N132 | pLTR-N6/T91/N132-L |

Plasmid p5'LTR-cat (ATCC No. 67904) was derived from pSV2-cat [Gorman et al., *Mol. Cell. Biol.* 2:1044–1051 (1982); ATCC No. 37155] by replacing the 259 base pair PvuII to HindIII fragment containing the SV40 origin region with a 650 base pair HpaI to HindIII 5'LTR-containing DNA fragment from the biologically active HIV proviral clone pHXB2gpt (obtained from A. Fisher, NIH, Bethesda, Md.) [Fisher et al., *Nature* 320:367-371 (1986)]. Plasmid p3'LTR-cat was constructed similarly using a 720 base pair XhoI to HindIII 3'LTR-containing DNA fragment from pHXB2gpt. The XhoI site was converted to a blunt end by Klenow reaction prior to ligation.

Plasmid pSV-tat (ATCC No. 67903) was derived from pSV-cat by replacing the HindIII to HpaI cat-containing fragment with a 2628 base pair SalI to BamHI fragment containing the HIV tat coding sequence from pHXB2gpt. Prior to ligation, the SalI site was converted to a HindIII site using a HindIII to SalI oligonucleotide linker and the BamHI site was converted to a blunt end by Klenow reaction.

Plasmid pLTR-IL2 was derived from p3'-LTR-cat by replacing the HindIII to HpaI cat-containing segment with a 400 base pair RsaI to StuI fragment containing the human IL2 coding sequence from plasmid pY3. Plasmid pY3 contains a human IL2 cDNA and was obtained from K. Livak (Du Pont Experimental Station, Wilmington, Del.). The IL2 coding sequence in pY3 is identical to that reported by Taniguchi et al., *Nature* 302:305-310 (1983).

Cell lines containing plasmids pTrpE-IL2, pTrpGk, pKGP36-trp, p5'LTR-cat and pSV-tat have been deposited at the American Type Culture Collection (ATCC), 12301 Parklawn Drive, Rockville, Md. 20852 U.S.A., under the terms of the Budapest Treaty. The ATCC accession numbers have been cited in the preceding text.

For the expression of glycosylated IL2 analogs we used HeLa cells as the host and the tat/LTR gene expression control signals derived from HIV-1. It would be well within the skill of the art to use techniques analogous to those described here to construct vectors for expression of desired coding sequences in alternative eukaryotic host cells. Expression vectors ordinarily include an origin of replication, a promoter and ribosome binding site located in front of the coding sequence to be expressed, and any necessary RNA splice sites, polyadenylation sites, and transcriptional terminator sequences. Other commonly available host cells and expression vectors may be used for the expression of glycosylated IL2 analogs in eukaryotic cells, including fungal cells, insect cells, plant cells and animal cells. Such methods for eukaryotic cell expression are reviewed in *Vectors: A Survey of Molecular Cloning Vectors and Their Uses*, Eds. Rodriguez and Denhardt, Butterworth, 1988. Particularly useful systems include systems employing a linked DHFR gene to obtain cell lines, for example, Chinese hamster ovary (CHO)-derived cell lines, with amplified copy number of the desired DHFR-linked gene by selection for resistance to methotrexate (Kaufman et al. (1986) *J. Biol. Chem.* 261:9622-9628; Patzer et al. (1986) *Biotechnology* 4:630-636).

Vectors for gene expression in plant and mammalian cells are commercially available from Clontech Laboratories, Palto Alto, Calif. Vectors for mammalian cell expression are also available from Pharmacia LKB Biotechnology Inc., Piscataway, N.J.

EXAMPLE 2

Expression in *E. coli* and Purification of IL2-derived Proteins

As described above, *E. coli* plasmid expression vectors containing the *E. coli* trp promoter were constructed. *E. coli* host strains MM294 and HB101, were used (Maniatis et al., *Molecular Cloning: A Laboratory Manual*, Cold Spring Harbor Laboratory, N.Y. (1982)). Expression from the trp operon promoter on the plasmid was carried out by growing a 5% inoculum (of an overnight culture in LB medium) in M9 minimal medium for 6 hours at 37° C.

Each of the IL2-derived proteins accumulated to high level in *E. coli*, representing approximately 5 to 10% of total *E. coli* protein. IL2-derived protein was solubilized from the *E. coli* host by suspension of the collected cells and sonication in high salt buffer containing 0.1% SDS. The *E. coli* expressed proteins, solubilized using 0.1% SDS and sonication, were analyzed by standard immunoblot (Western Blot) methods. Immunoblot indicated that the various IL2 analogs were expressed at approximately the same level in *E. coli*.

EXAMPLE 3

TCGF Activity of *E. coli*-expressed IL2-Derived Proteins

The TCGF bioactivity of IL2 was measured using the IL2-dependent murine T-cell line CTLL-2 (Gillis and Smith (1977) *Nature* 268, 154-156). These cells grow only in the presence of IL2, and their growth is directly proportional to the IL2 activity in the cultures. The overnight growth of CTLL cells in the presence of varying amounts of IL2 can be measured by either the uptake of [methyl-$^3$H]thymidine (Gillis et al. (1978) *J. Immunol.* 120, 2027-2032) or by the cells' ability to metabolize the dye MTT (Mosman (1983) *J. Immunol. Meth.* 65, 55). Typically, 20,000 CTLL-2 cells are plated in 96-well microtiter plates in medium either lacking IL2 or containing serially diluted concentrations of a standardized IL2 preparation. One unit of TCGF activity was defined as the reciprocal of the dilution that yielded half-maximal incorporation of [methyl-$^3$H]-thymidine or optical density change of MTT. Unknown IL2 preparations are measured against a standard curve of standard IL2 on a logit plot (Robb (1985) *Meth. Enzymol.* 116:493-525). Purified human Jurkat cell-derived IL2 has a specific activity of approximately 0.31 units (U) per ng using the assays performed here. For *E. coli*-expressed IL2 samples, serial dilutions were prepared from supernatants of the total cell lysate as prepared using 0.1% SDS and sonication. For mammalian cell-expressed IL2, cell culture medium was used in the assay.

IL2 protein was quantitated using a commercial ELISA (enzyme linked immumosbsorption assay) marketed by Genzyme. In this assay, IL-2 is reacted with an anti-human-IL-2 mouse monoclonal antibody bound on the surface of a microtitre plate. Anti-human-IL-2 polyclonal rabbit antibody is reacted with the bound IL-2. Rabbit antibody is quantified by the use of enzyme-conjugated goat anti-rabbit-immunoglobulin. In this case, the enzyme is horse-radish peroxidase and the amount of color developed is proportional to the amount of bound IL-2. A standard curve is prepared in the range of 60 to 0.5 U per mL and the unknown is compared to this. Knowing the U/mL value allows determination of the concentration of IL2 (ng/mL).

Tables 6 and 7 show the IL2 TCGF bioactivity of various *E. coli*-expressed and human cell-expressed IL2 analogs. Data are shown in Table 6 but not in Table 7 for IL2-N6/T80-L because it was expressed in *E. coli* but was not expressed at detectable level in mammalian cells. We expect that mammalian cell expressed IL2-N6/T80-L would have similar activity to IL2-N6/T80, which was expressed in mammalian cells. As shown in Table 6, *E. coli*-expressed IL2 analogs N6, S29, T80, N6/T80, T91, and N132 are approximately equivalent to or exceed that of r-IL2 (native sequence) in relative TCGF activity.

TABLE 6

| TCGF Activity of IL2 Analogs Expressed in *E. coli* | | | |
|---|---|---|---|
| | ELISA | | TCGF Activity |
| IL2 | U/mL | ng/mL | U/mL | U/ng |
| r-IL2 | 120.0 | 384.0 | 17.2 | 0.1 |
| IL2-N6-L | 105.0 | 336.0 | 135.3 | 0.4 |
| IL2-S29-L | 96.0 | 307.2 | 27.8 | 0.09 |
| IL2-T80-L | 940.0 | 3008.0 | 3169.8 | 1.05 |
| IL2-N6/T80-L | 1400.0 | 4480.0 | 707.6 | 0.16 |
| IL2-T91-L | 1000.0 | 3200.0 | 611.8 | 0.19 |
| IL2-N132-L | 1400.0 | 4480.0 | 495.5 | 0.11 |

TABLE 7

| TCGF Activity and LAK Inducing Activity of IL2 Analogs Mammalian Cell Expressed | | | | | |
|---|---|---|---|---|---|
| | ELISA | | TCGF | | LAK | |
| MUTANT | U/mL | ng/mL | U/mL | U/ng | U/mL | U/ng |
| IL2-N6 | 31.0 | 99.2 | 41.9 | 0.4 | 2.0 | 0.02 |
| IL2-N6/S29 | 1.5 | 4.8 | 0.0 | 0.0 | 0.04 | 0.008 |
| IL2-N6/T80 | 1.3 | 4.2 | 1.6 | 0.4 | 0.4 | 0.1 |
| IL2-N6/T91 | 10.0 | 32.0 | 2.0 | 0.06 | 1.0 | 0.03 |
| IL2-N6/N132 | 40.0 | 128.0 | 32.4 | 0.25 | 10.0 | 0.078 |
| IL2-N6/T91/N132 | 60.0 | 192.0 | 18.8 | 0.1 | 4.0 | 0.021 |
| IL2-N6-L | 42.0 | 134.4 | 20.8 | 0.16 | 10.0 | 0.074 |
| IL2-N6/S29-L | 13.0 | 41.6 | 0.2 | 0.005 | 0.8 | 0.02 |
| IL2-N6/T91-L | 0.9 | 2.9 | 0.9 | 0.3 | 0.1 | 0.034 |
| IL2-N6/N132-L | 0.9 | 2.9 | 0.7 | 0.24 | 0.1 | 0.034 |
| IL2-N6/T91/N132-L | 7.8 | 25.0 | 4.7 | 0.19 | 0.02 | 0.001 |

EXAMPLE 4

Generation of Lumphokine-activated Killer (LAK) Cell Activity in Human Peripheral Blood Lymphocytes Human peripheral blood lymphocytes were obtained by Ficoll-Hypaque centrifugation (Boyum, op. cit.) and incubated in the presence of samples containing 10 TCGF U/mL of r-IL2, L-IL2, and the other IL2 analogs, both *E. coli*-expressed and human cell-expressed for 3 to 4 days. LAK cell cytotoxicity of the cultured cells was measured using $^{51}$Cr-labeled Raji cells (ATCC #CCL-86) as targets in a 4-hour assay or europium-labeled Raji cells in a 1-hour assay. Cell killing is assessed in this assay by the release of $^{51}$Cr or europium from the labeled Raji target cells. Results were derived by keeping the effector to target cell ratio constant, by controlling the amount of NK killing by the use of NK-sensitive target K562 cells, and by titrating the amount of IL-2 used in the activation. Activation by standard preparations of IL-2 were compared with the unknowns to derive the units per milliliter and, hence, the units per nanogram. Purified r-IL2 has an activity of approximately 0.3 units per nanogram, irrespective of the assay used.

The E. coli-expressed IL2 analogs N6, S29, T80, N6/T80, T91, and N132 exhibited LAK induction activity approximately equivalent to that of r-IL2 (native sequence). As shown in Table 8, the various mammalian cell-expressed IL2 analogs are also capable of inducing LAK activity in human peripheral blood lymphocytes.

EXAMPLE 6

Mammalian Cell Transfection, Growth and Selection

Mammalian cell lines were maintained as monolayer cultures in Dulbecco's modified minimal Eagle's medium (DMEM) with high glucose and supplemented with 10% calf serum (Hazleton Research Products, Denver, Pa.). Cells were plated at $5 \times 10^5$ cells per 60 mm tissue culture dish and were transfected the next day using the calcium phosphate co-precipitation procedure [Graham and Van der Eb, Virology 52:456–467 (1973); Wigler et al., Proc. Natl. Acad. Sci. U.S.A. 76:1373–1376 (1979)].

For mammalian expression of IL2 and IL2 analogs, 20 μg of the IL2-mammalian-expression plasmid DNA (for example, pLTR-IL2 or pLTR-N6) was cotransfected with 5 or 10 μg pSV-tat plasmid DNA into 2 to $5 \times 10^6$ cells seeded on P100 plates the previous night. Cells were allowed to grow for 40 to 48 hours (at 37° C., 5% CO$_2$) following transfection and the cell culture medium was assayed for IL2.

The proportion of glycosylated IL2 protein in the HeLa-expressed IL2 was determined by Western blot analysis and estimating the amounts of IL2 present in the various higher-molecular-weight bands compared to that present in the position of unglycosylated IL2. Treatment of the IL2 samples with endoglycosylase prior to the Western blot analysis confirmed that the shift in gel mobility (reduced mobility) of the IL2 proteins was attributable to glycosylation of the primary product.

The relative distribution of glycosylated forms of IL2 and non-glycosylated IL2 for each of the IL2 analogs tested is shown in Table 8. The results indicate that the N-linked glycosylation sites introduced into the IL2 protein are effectively recognized and glycosylated in mammalian cells.

TABLE 8

| Glycosylation Pattern of Hela Cell Expressed IL2 Analogs | | |
|---|---|---|
| IL2 Analog | Non-Glycosylated | Glycosylated |
| IL2-N6 | 60 | 40 |
| IL2-N6/S29 | 20 | 80 |
| IL2-N6/T80 | 50 | 50 |
| IL2-N6/T91 | 90 | 10 |
| IL2-N6/N132 | 65 | 35 |

TABLE 8-continued

| Glycosylation Pattern of Hela Cell Expressed IL2 Analogs | | |
|---|---|---|
| IL2 Analog | Non-Glycosylated | Glycosylated |
| IL2-N6/T91/N132 | 70 | 30 |

Table 9

L-IL2 Coding Sequence and Encoded Amino Acid Sequence

The position of the first base of the recognized restriction site is indicated. The number of the polypeptide begins with the Met of the E. coli-expressed protein; the N-terminal Ala of native mature human IL-2 is designated amino acid number 2.

The residues that are changed in the various IL2 analogs of this invention are underlined. In pTrpGk, the ATG is preceded by a HindIII restriction site:

```
HindIII
|
AGCTT ATG ...
```

```
            10                          30
 1  A TGGCTCCTACTTCAAGTTCTACAAAGAAA     30
 1M   A  P  T  S  S  S  T  K  K        10
                  -     -

50
 31 ACACAGCTACAACTGGAGCATTTACTGCTG      60
11T    Q  L  Q  L  E  H  L  L  L       20

70                          90
 61 GATTTACAGA TGATTTTGAATGGAATTAAT     90
21D    L  Q  M  I  L  N  G  I  N       30
                                  -

110
 91 AATTACAAGAATCCCAAACTCACCAGGA TG    120
31N    Y  K  N  P  K  L  T  R  M       40
                     -

130                        150
121 CTCACATTTAAGTTTTACA TGCCCAAGAAG    150
41L    T  F  K  F  Y  M  P  K  K       50
                                  -

170
151 GCCACAGAACTGAAACATCTTCAGTGTCTA    180
51A    T  E  L  K  H  L  Q  C  L       60

190                        210
181 GAAGAAGAACTCAAACCTCTGGAGGAAGTG    210
61E    E  E  L  K  P  L  E  E  V       70

230
211 CTAAATTTAGCTCAAAGCAAAAACTTTCAC    240
71L    N  L  A  Q  S  K  N  F  H       80
               -                 -

250                        270
241 TTAAGACCCAGGGACTTAATCAGCAATATC    270
81L    R  P  R  D  L  I  S  N  I       90
                        -

290
271 AACGTAATAGTTCTGGAACTAAAGGGATCT    300
91N    V  I  V  L  E  L  K  G  S      100
   -     -                        -
```

-continued

```
                 310                      330
301 GAAACAACATTCATGTGTGAATATGCTGAT 330
101 E   T   T   F   M   C   E   Y   A   D   110

350
331 GAGACAGCAACCATTGTAGAATTCCTGAAC 360
111 E   T   A   T   I   V   E   F   L   N   120

370                      390
361 AGAT GGATTACCTTTTGTCAAAGCATCATC 390
121 R   W   I   T   F   C   Q   S   I   I   130

Kpn 1              410
391 TCAACAGGTACCGGAGGAGGTAAGAAGGAT 420
131 S   T   G   T   G   G   G   K   K   D   140

430     Bam H1           450
421 AAGAAGGATAAGAAGGATCTCGAGTGATAA 450
141 K   K   D   K   K   D   L   E   *   *   148

Sma 1
451 CCCGGGATCC 460
```

We claim:

1. A recombinant IL2 analog which has substantially the same spectrum of biological activity and substantially the same amino acid sequence as native human mature IL2, but which differs from native human mature IL2 in that it has one or more amino acid substitutions to provide one or more N-linked glycosylation sites NXT or NXS, wherein X is any amino acid except D, W or P, characterized in that the N of the glycosylation site or sites occurs at one or more of amino acid positions 6, 29, 80, 91, and 132, wherein the position numbers correspond to the numbers for r-IL2 as shown in TABLE 1.

2. Recombinant IL2 analog of claim 1 wherein the N-glycosylation site is glycosylated.

3. Recombinant IL2 analog of claim 1 or 2 wherein N is substituted for S at position 6.

4. Recombinant IL2 analog of claim 1 or 2 wherein S is substituted for I at position 29.

5. Recombinant IL2 analog of claim 1 or 2 wherein T is substituted for H at position 80.

6. Recombinant IL2 analog of claim 1 or 2 wherein T is substituted for N at position 91.

7. Recombinant IL2 analog of claim 1 or 2 wherein N is substituted for T at position 132.

8. Recombinant IL2 analog of claim 1 or 2 wherein N is substituted for S at position 6 and S is substituted for I at position 29.

9. Recombinant IL2 analog of claim 1 or 2 wherein N is substituted for S at position 6 and T is substituted for H at position 80.

10. Recombinant IL2 analog of claim 1 or 2 wherein N is substituted for S at position 6 and T is substituted for N at position 91.

11. Recombinant IL2 analog of claim 1 or 2 wherein N is substituted for S at position 6 and N is substituted for T at position 132.

12. Recombinant IL2 analog of claim 1 or 2 wherein N is substituted for S at position 6, T is substituted for N at position 91 and N is substituted for T at position 132.

* * * * *